United States Patent
Vaabengaard et al.

(10) Patent No.: US 6,558,792 B1
(45) Date of Patent: May 6, 2003

(54) PRESSURE SENSITIVE ADHESIVE COMPOSITION

(75) Inventors: Rikke Vaabengaard, Tisvildeleje (DK); Danuta Ciok, Nivaa (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 09/926,162

(22) PCT Filed: Mar. 17, 2000

(86) PCT No.: PCT/DK00/00129

§ 371 (c)(1),
(2), (4) Date: Sep. 17, 2001

(87) PCT Pub. No.: WO00/54820

PCT Pub. Date: Sep. 21, 2000

(30) Foreign Application Priority Data

Mar. 17, 1999 (DK) .......................... 1999 00377

(51) Int. Cl.⁷ .......................... B32B 15/04; B32B 7/12
(52) U.S. Cl. .......................... 428/355 CP; 428/355 R; 428/356; 428/355 RA; 524/9; 524/47; 523/105; 523/111; 523/120
(58) Field of Search ................. 523/120, 105, 523/111; 524/1, 9, 10, 13, 14, 47, 55; 424/77; 428/355 R, 356, 355 RA, 355 CP, 355 BL, 355 N

(56) References Cited

U.S. PATENT DOCUMENTS

| 3,339,546 A | 9/1967 | Chen | 128/156 |
|---|---|---|---|
| 4,253,460 A | 3/1981 | Chen et al. | 128/283 |
| 4,551,490 A | * 11/1985 | Doyle et al. | 428/355 BL |
| 5,466,724 A | 11/1995 | Volke et al. | 523/111 |
| 5,492,943 A | * 2/1996 | Stempel | 523/111 |
| 5,827,528 A | * 10/1998 | Kubo et al. | 424/443 |

FOREIGN PATENT DOCUMENTS

| DE | WO 9951189 | * 10/1999 | ............ A61K/6/00 |
|---|---|---|---|
| GB | 2 300 195 | 10/1996 | |
| JP | 10130164 | 5/1998 | |
| WO | 97/30093 | 8/1997 | |
| WO | 99/11302 | 3/1999 | |

* cited by examiner

Primary Examiner—James J. Seidleck
Assistant Examiner—Travis B Ribar
(74) Attorney, Agent, or Firm—Jacobson Holman PLLC

(57) ABSTRACT

A pressure sensitive adhesive composition suitable for medical purposes comprising a rubbery elastomeric base and water soluble or water swellable hydrocolloids, where the adhesive composition includes a substantially homogeneous mixture of 15–60% of one or more rubbery components, 10–60% of a mixture of hydrocolloids that includes a cellulose derivative, amidated pectin, and potato starch, 0–50% of one or more tackifier resins, 0–15% cohesive strengthening agent, 0–10% of a plasticizer and 0–5% pigment. The adhesive shows at least as good properties as state of the art adhesives comprising gelatine with respect to resistance to biological fluids, adhesion to skin, and coherence.

17 Claims, No Drawings

PRESSURE SENSITIVE ADHESIVE COMPOSITION

This is a nationalization of PCT/DK00/00129, filed March 17, and published in English. This application is to be prosecuted on the basis of originally filed Chapter I claims.

FIELD OF THE INVENTION

The present invention relates to pressure sensitive adhesive compositions suitable for various medical applications and especially suitable for use for adhesion to the skin, in particular in the field of ostomy care. More specifically, this invention relates to adhesive compositions comprising a rubbery elastomeric base and two or more water soluble or water swellable hydrocolloids are dispersed therein, the use of such adhesive compositions for the preparation of a wound dressing or an adhesive wafer for an ostomy appliance, and to wound dressings or ostomy appliances comprising such adhesive composition and a mixture of hydrocolloids.

BACKGROUND OF THE INVENTION

In connection with surgery for a number of diseases in the gastrointestinal tract a consequence is, in many cases, that the colon, the ileum or the urethra has been exposed surgically and the patient is left with an abdominal stoma and the effluents or waste products of the body, which are conveyed through these organs, are discharged through the artificial orifice or opening and are collected in a collection bag, which is usually adhered to the skin by means of an adhesive wafer or plate having an inlet opening for accommodating the stoma. Also in connection with a fistula, the patient will have to rely on an appliance to collect the bodily material emerging from such opening.

In connection with treatment of wounds, it is often desirable to cover and protect the wound with a skin barrier or dressing comprising a backing and an adhesive layer for contacting the wound and the surroundings for ensuring a bacteria-tight closure of the wound.

Various skin adhesive agents are used today for the above mentioned purposes.

Such adhesives should have a composition which is sufficiently tacky to secure the appliance or skin barrier to the abdomen, and a cohesion ensuring safe removal thereof without leaving residues on the skin. Furthermore, the adhesive should show a degree of elasticity to enable the adhesive layer of the appliance or barrier to follow the movements of the patient without slipping the skin and should also show a great resistance to erosion caused by aggressive exudates from an ostomy in order to minimise the risk of leakage. Still further, no adverse reactions or effects should be inflicted upon the user from using the adhesives.

A very widespread embodiment of skin adhesive agents comprises a self-adhesive elastomeric matrix, in which water-absorbing, swelling particles, the so-called hydrocolloids, are dispersed.

Adhesive compositions comprising hydrocolloids have been known for many years. U.S. Pat. No. 3,339,549 discloses a blend of a rubbery elastomer such as polyisobutylene and one or more water soluble or water swellable hydrocolloids such as a powdery mixture of pectin, gelatine and carboxymethylcellulose. The adhesive mass has a water-insoluble film applied to one surface. A composition of this type is available commercially from E. R. Squibb & Sons Inc. under the trademark "Stomahesive" and is used as a skin barrier around stomas to prevent skin breakdown by the corrosive fluids discharged by the stoma.

In adhesive compositions of this type, the polyisobutylene is responsible for provision of the adhesive properties and the dispersed hydrocolloid powders absorb fluid and render the adhesive agent capable of also adhering to moist skin (wet tack). These compositions are also gaining increasing acceptance as wound dressings for dermal ulcers, burns and other exuding wounds.

WO 97/30093 (Hercules Incorporated) discloses polyvalent cation crosslinked pectin fibre composition composed of a calcium sensitive methoxyl pectin with a degree of esterification of less than 15% or calcium sensitive amidated pectin having a degree of esterification of less than 50% where the pectin is polyvalent cation crosslinkable and has an average molecular weight having an upper limit of 200,000 and a lower limit of 5000. The fibres are stated to be useful in making of wound dressings as a part of a gauze material. One major problem which has been encountered with conventional adhesive compositions comprising hydrocolloids is their susceptibility to breakdown upon exposure to body fluids. When the compositions are used as skin barriers, e.g., around stomas, absorption of fluid is desirable, but excessive swelling causes the composition to lose its integrity opening for leaks and the barrier must be replaced more often than is desirable from a skin protection point of view, and very often, a residue remains on the skin, which in many cases is difficulty to remove. Furthermore, an increased awareness has developed with respect to avoiding constituents which could be a potential risk of transferring infectious diseases using material of animal origin.

A number of attempts have been made to improve the integrity of adhesive compositions.

As a method for improving the adhesive integrity the use of hydrocolloids has been described which, in themselves, are cross-linked (e.g. cross-linked carboxymethylcellulose (CMC), cross-linked dextran and other water-absorbing, but insoluble hydrocolloids). They will not dissolve due to the cross-linked structure. During the swelling process the individual particles will, therefore, obtaining a gel-like structure, but no coherent gel could be formed since the macromolecules of the cross-linked hydrocolloids are locked in the gel network constituted by the individual particles. Due to the lack of a coherent gel, the cross-linked hydrocolloids may be leached out and suspended in the body fluids and the effect on the integrity of the swelled adhesive, therefore, is limited.

Generally speaking, these prior methods improve the integrity of adhesive compositions. Nevertheless, a need still exists for an improved adhesive composition showing resistance to biological fluids as well as improved properties of adhesion to the skin.

Now it has been found that it is possible to provide an improved adhesive composition showing at least as good resistance to biological fluids as well as adhesion to the skin and integrity in the form of improved coherence as state of the art adhesives without having to rely on material of animal origin, especially gelatine.

BRIEF DESCRIPTION OF THE INVENTION

The present invention relates to a pressure sensitive adhesive composition suitable for various medical applications and especially suitable for use for adhesion to the skin, in particular in the field of ostomy care, which adhesive composition comprises a rubbery elastomeric base and two or more water soluble or water swellable hydrocolloids dispersed therein.

Furthermore, the invention relates to ostomy appliances comprising such adhesive compositions and the use of such adhesive compositions for preparing wound dressings or ostomy appliances.

Still further, the invention relates to a mixture of hydrocolloids suitable for inclusion in pressure sensitive skin-friendly adhesives.

DETAILED DESCRIPTION OF THE INVENTION

The present invention relates to a pressure sensitive adhesive composition suitable for medical purposes comprising a rubbery elastomeric base and two or more water soluble or water swellable hydrocolloids, said adhesive composition comprising a substantially homogeneous mixture of 15–60% of one or more rubbery components, 20–60% of a mixture of hydrocolloids comprising one or more hydrocolloids selected from the group of amidated pectins and potato starch, 0–50% of one or more tackifier resins, 0–10% of a plasticizer and 0–5% pigment.

By introducing a combination of hydrocolloids particles comprising amidated pectin and/or potato starch, constituents of animal origin are avoided, and at least as good integrity of the hydrocolloid adhesive and gel integrity are achieved together with a good cohesion and absorption of water as compared with the state of the art adhesives comprising gelatine. Thus, a very commonly used hydrocolloid, gelatine, showing good absorbing capacity and integrity of the adhesive after absorption and which may carry infectious diseases of animal origin may be substituted without loosing absorption capacity and, at the same time, the absorption of water is upheld without leading to breakdown of the structure of the adhesive. The amidated pectin used in accordance with the invention has a degree of esterification above 50%, suitably about 54% or above.

The amidated pectin to be used according to the invention suitably shows a degree of amidation of form about 2 to about 7%, more preferred from about 4 to about 6%, most preferred about 5%.

The amidated pectin is present in the form of particles which are preferably mixed homogeneously in the adhesive composition.

WO 97130093 does not disclose not indicate preparation of hydrocolloid particles nor incorporation of such particles in adhesive compositions as a part of a hydrocolloid constituent. Furthermore, the amidated pectins disclosed in WO 97/30093 have a degree of esterification of less than 50% whereas the particles of amidated pectin used according to the present invention has a degree of esterification above 50%.

A preferred adhesive composition according to the invention comprises a substantially homogeneous mixture of 30–60% of one or more rubbery components, 30–60% of a mixture of hydrocolloids comprising one or more hydrocolloids selected from the group of amidated pectins and potato starch, 0–25% of one or more tackifier resins, 0–10% of cohesive strengthening agent, 0–10% of a plasticizer and 0–5% pigment.

It is preferred that the mixture of hydrocolloids used according to the invention comprises a cellulose derivative (e.g. salts of carboxymethylcellulose, methylcellulose and hydroxypropylmethylcellulose), carboxymethylecellulose (CMC). A preferred are cellulose derivative is CMC.

Further hydrocolloids may be included in the mixture of hydrocolloids used according to the invention such as guar gum, locust bean gum (LBG), pectin, alginates, xanthan or karaya, semisynthetic hydrocolloids such as sodium starch glycolate and synthetic hydrocolloids such as polyvinylalcohol or polyethylene glycol.

Amidated pectin and CMC provides a strong gel integrity. Compositions of the invention exhibit greater resistance to degradation by biological fluids than comparable adhesive compositions of the prior art. Furthermore, no residue of the adhesives of the invention remains on the skin upon removal of the adhesive.

Without limiting the invention to any specific hypothesis, it is presumed that the improvement in integrity associated with the composition of the present invention is to be attributed to a linkage or bond between different molecular chains and depends on both hydrogen bonds created by the amidated ester groups and calcium bridges created by $Ca^{2+}$-ions.

The best results are obtained with a mixture of amidated pectin, CMC and optionally potato starch. Potato starch comprises amylose and amylosepectin polymers.

It is preferred according to the invention that the mixture of hydrocolloids consist of amidated pectin, potato starch, and a cellulose derivative.

The total amount of hydrocolloids are 40–80% of the total composition when a conjugated butadiene polymer is used and 20–40% when a block-copolymer combination is used.

The rubbery component or components used in the adhesive of the invention may be a conjugated butadiene polymer such as polybutadiene, polyisobutylene or polyisoprene, preferably polyisobutylene.

A cohesive strengthening agent may suitably be a physically cross-linked elastomer selected from block-copolymers of styrene, a chemically cross-linked natural or synthetic rubbery elastomer and/or a rubbery homopolymer, optionally together with a plasticizer or a tackifier resin.

A physically cross-linked elastomer selected from block-copolymers comprising styrene and one or more butadienes may be a styrene-butadiene-styrene copolymer, a styrene-isoprene copolymer and is preferably a mixture of styrene-isoprene-styrene and styrene-isoprene copolymer.

A chemically cross-linked rubbery elastomer may e.g. be butyl rubber or natural rubber.

A rubbery homopolymer may be a polymer of a lower alkene such as low density polyethylene or propylene, preferably atactic polypropylene (APP).

A tackifying resin optionally used in accordance with the invention is preferably a hydrocarbon tackifier resin and is more preferred selected from the group comprising polymers and copolymers of cyclopentadiene, dicyclopentadiene, alpha-pinene or beta-pinene.

A cohesive strengthening agent may suitably be a physically crosslinked elastomer comprising a styrene-butadiene-styrene copolymer or a styrene-isoprene-styrene copolymer. Such copolymers may preferably comprise 0–10% of a plasticizer, preferably dioctyl adipate.

The adhesive compositions of the invention may optionally comprise further components normally used in formulation of adhesive compositions such as pigments such as zinc oxide or titanium dioxide. Pigments may be present in amount up to about 5% and will typically be present in an amount of 2–4%.

In a further aspect, the invention relates to the use of an adhesive composition comprising a rubbery elastomeric base and one or more water soluble or water swellable hydrocolloids, said adhesive composition comprising a substantially homogeneous mixture of 15–60% of one or more rubbery components, 20–60% of a mixture of comprising one or more hydrocolloids selected from the group of amidated pectins and potato starch, 0–50% of one or more tackifier resins, 0–15% cohesive strengthening agent, 0–10% of a plasticizer and 0–5% pigment for securing ostomy appliances to the skin and for sealing around an ostomy, for securing wound dressings or wound drainage bandages to the skin, for securing devices for collecting urine to the skin , or for securing orthoses or prostheses to the skin.

In a still further aspect, the invention relates to an ostomy appliance for placing on the abdomen of a patient for use in collecting discharge of visceral contents comprising an adhesive composition containing a substantially homogeneous mixture of 15–60% of one or more rubbery components, 15–50% of one or more tackifier resins, and 20–60% of a mixture of hydrocolloids comprising one or more hydrocolloids selected from the group of amidated pectins and potato starch.

The ostomy appliance according to the invention may be an open or a closed appliance suitable for use in connection with a colostomy, an ileostomy or a urostomy. It may be a one-piece appliance or a body side member or face plate forming part of a two-piece appliance comprising the body side ostomy member and a separate collection bag and optionally comprising a convex member. A separate collection bag may be attached to the body side member in any convenient manner known per se, e.g. via a coupling ring or by a flange covered with an adhesive.

An ostomy appliance according to the invention may be made from materials conventionally used for the preparation of ostomy appliances in a manner known per se in the field.

In yet a further aspect, the invention relates to a mixture of hydrocolloids suitable for inclusion in pressure sensitive skin-friendly adhesives, said mixture comprising one or more hydrocolloids selected from amidated pectins and potato starch.

The mixture of hydrocolloids of the invention preferably comprises an amidated pectin and CMC providing a superior capacity for absorbing water.

The invention is illustrated more in detail in the below Examples disclosing embodiments of the invention.

Materials and Methods

PIB: Polyisobutylene available under the trademark Vistanex from Exxon Chemical Co. as grade LM-MH.

Butyl Rubber: Polysar Butyl 101-3 from Bayer AG.

Kraton D1107: Styrene-isoprene-styrene copolymer having a molecular weight of 212,000–260,000 (GPC) and a content of diblock 15–25%

Vestoplast: APP (ataktisk polypropylene) viscosity at 190° C. 19.000–25.000 mpas from Hüls AG.

Arkon 90: Hydrogenated cyclopentadiene tackifier from Arakawa Forest hemical industries Ltd.

CMC: Sodium carboxymethylcellulose available from Akzo under the tradename Akucell® AF2881

Amidated pectin: X-8906 LM, AS Conf., X-8907 LM 102 AS., X-8908 LM 104 AS-REV. from Hercules.

Potato starch: Kartoffelmes produced by Cerestar for Dansk Supermarked, DVN 1006.4

A Z mixer Type LKB 025 from Herman-Linden was used.

Water Absorption Measurement

The adhesive to be tested was pressed into a plate with a thickness of 1 mm. A sample of 25×25 mm was then punched out and adhered on an object glass. The object glass with the sample was weighed and placed in a beaker with 0.9% isotonic saline at 37° C. After 2 hours, the object glass with the sample was removed form the beaker, dried on the surface, and weighed again. The increase of weight was recorded as the water absorption.

Leaching of Adhesives

Leaching out of adhesives was tested using a cylindric leaching for 8 hours using 0.9% saline.

Gel Strength Measurement

The adhesive to be tested was pressed into a plate with a thickness of 1 mm. A sample with an diameter of 50 mm was punched out and adhered on a φ80 mm Petri dish. 0.9% isotonic saline was poured into the Petri dish until the sample is totally covered. A lid was put on. After 18 hours, the sample were evaluated for their gel strength according to an internal system using five reference adhesives having different gel strengths.

DMA (Dynamic Mechanical Analysis) Test

A DMA analysis was carried out for sample 1 and 2. The analysis was carried out by using a Haake RS150 apparatus with a sensor of 8 mm plate/plate. A frequency sweep was run for samples 1 and 2 at a temperature of 32° C. and frequency of 1 Hz.

Experimental Part

EXAMPLE 1

Preparation of an adhesive material according to the invention comprising PIB and having the composition stated in the below Table 1:

TABLE 1

| Ingredient | Percent by weight |
|---|---|
| PIB | 40 |
| Amidated Pectin | 27.5 |
| Potato starch | 5 |
| CMC | 27.5 |

80 grams of PIB was added to the Z mixer at 80° C. and softened for about 10 minutes under a vacuum of 50 mbar. Then, the vacuum was released and 55 grams of amidated pectin, 55 grams of CMC and 10 grams of potato starch were added and mixed for 15 minutes and the mixing was continued under vacuum of 50 mbar until a homogeneous dough-like mass was formed.

This dough-like mass was then removed from the mixer while hot and soft and formed into approximately 1 mm thick sheet stock material by compression moulding the adhesive mass at approximately 90° C. and 100 Bars between two sheets of silicone paper. The resultant flat plate was cut into the desired shapes.

EXAMPLES 2–4

In an analogous manner as disclosed in Example 1 adhesive compositions according to the invention having the compositions in percent by weight stated in the below Table 2 were prepared (table 2 and 3):

TABLE 2

| Ingredient | Example 2 | Example 3 | Example 4 |
|---|---|---|---|
| PIB | 40 | 60 | 40 |
| Amidated Pectin | 25 | 15 | 30 |
| Potato starch | 10 | 10 | |
| CMC | 25 | 15 | 30 |

EXAMPLE 5

Preparation of an adhesive material according to the invention comprising PIB and SIS and having the composition stated in the below Table 3:

TABLE 3

| Ingredient | Percent by weight |
| --- | --- |
| PIB | 40 |
| Kraton D1107 (SIS) | 10 |
| Zinc oxide | 3 |
| Amidated Pectin | 16 |
| Potato starch | 15 |
| CMC | 16 |

100 grams of PIB was added to a Z mixer at 150° C. and softened for 5 minutes. Then 100 grams of Kraton was added and mixing was continued at 150° C. and 50 mbar until the blend was homogeneous. The mass was cooled to 80° C. 160 grams of mass were taken away from the mixer, and 60 grams of PIB, 6 grams zinc oxide, 32 grams of amidated pectin, 30 grams of potato starch and 32 grams of CMC were added to the mixer. Mixing was continued under 80° C. and 50 mbar until a homogeneous dough-like mixture was obtained.

This dough-like mass was then removed from the mixer while hot and soft and formed into approximately 1 mm thick sheet stock material by compression moulding the adhesive mass at approximately 90° C. and 100 Bars between two sheets of silicone paper. The resultant flat plate was cut into the desired shapes.

EXAMPLE 6

In an analogous manner as disclosed in Example 1 an adhesive composition stated in the below table 4 was prepared. APP was added together with PIB in the beginning of the mixing. Zinc oxide was added together with the hydrocolloids.

TABLE 4

| Ingredient | Percent by weight |
| --- | --- |
| PIB | 40 |
| APP | 10 |
| Zinc oxide | 3 |
| Amidated Pectin | 18.5 |
| Potato starch | 10 |
| CMC | 18.5 |

EXAMPLE 7

Preparation of an adhesive composition according to the invention comprising PIB and butyl rubber and having the composition stated in the below Table 5.

TABLE 5

| Ingredient | Percent by weight |
| --- | --- |
| PIB | 30 |
| Butyl Rubber | 15 |
| Arkon P90 | 10 |
| Amidated Pectin | 15 |
| Potato Starch | 15 |
| CMC | 15 |

75 grams of butyl rubber was added to a Z mixer at 150° C. and softened for 5 minutes. Then 50 grams of Arkon P90 and 75 grams of PIB were added and mixing was continued at 150° C. and 50 mbar until the blend was homogeneous. The mass was cooled to 80° C., and 120 grams of mass was taken away from the mixer. Then 30 grams of PIB, 30 grams of amidated pectin, 30 grams of potato starch and 30 grams of CMC were added into the mixer. Mixing was continued under 80° C. and 50 mbar until a homogeneous dough-like mixture was obtained.

This dough-like mass was then removed from the mixer while hot and soft and formed into approximately 1 mm thick sheet stock material by compression moulding the adhesive mass at approximately 90° C. and 100 Bars between two sheets of silicone paper. The resultant flat plate was cut into the desired shapes.

EXAMPLE 8

For comparison adhesives according to the invention comprising PIB and, as hydrocolloids, amidated pectin and potato starch and corresponding adhesives comprising, as hydrocolloids, pectin and gelatine and having the compositions stated in the below Table 6 were prepared in an analogous manner as disclosed in Example 1, and zinc oxide was optionally added before the hydrocolloids in analogy with the procedure disclosed in Example 5.

TABLE 6

| Ingredient | Percent by weight | | |
| --- | --- | --- | --- |
| Mixture | A1 | A2 | Comp A |
| PIB | 40 | 40 | 40 |
| Amidated Pectin | 20 | 25 | |
| Potato Starch | 25 | 20 | |
| CMC | 15 | 15 | 20 |
| Pectin | | | 19.5 |
| Gelatine | | | 20 |
| Zinc Oxide | | | 0.5 |

The water absorption, and the gel strength were tested and DMA was carried out for comparing adhesive compositions according to the invention with adhesive compositions of the state of the art.

The results of the tests for water absorption and gel strength are summarised in the below Table 7.

TABLE 7

| Sample | Water absorption | Gel strength |
| --- | --- | --- |
| A1 | 0.32 g/cm$^2$/2-hrs | 2 |
| A2 | 0.30 g/cm$^2$/2-hrs | 3 |
| Comp A | 0.29 g/cm$^2$/2-hrs | 2 |

The results of the DMA showed that the the tangens delta of the compositions are at the same level for all three adhesives whereas the complex shear modulus G' [Pa] is slightly greater for samples A1 than for Comp A. No data are available for sample A2. No difference in leaching out was found.

Thus, it appears that the adhesives of the invention shows at least the same absorption of water retaining the same gel strength as the adhesive of the state of the art.

EXAMPLE 9

For comparison adhesives according to the invention comprising PIB and SIS and, as hydrocolloids, amidated pectin and potato starch and corresponding adhesives comprising, as hydrocolloids, pectin and gelatine and having the compositions stated in the below Table 8 were prepared in an analogous manner as disclosed in Example 5.

TABLE 8

| Ingredient | Percent by weight | | |
|---|---|---|---|
| Mixture | B1 | B2 | Comp B |
| PIB | 40 | 40 | 40 |
| Kraton D1107 (SIS) | 10 | 10 | 10 |
| Amidated Pectin | 20 | 25 | |
| Potato Starch | 10 | 5 | |
| CMC | 20 | 20 | 22.5 |
| Pectin | | | 10 |
| Gelatine | | | 17.5 |

The water absorption, and the gel strength were tested and DMA was carried out for comparing adhesive compositions according to the invention with adhesive compositions of the state of the art.

The results of the tests for water absorption and gel strength are summarised in the below Table 9.

TABLE 9

| Sample | Water absorption | Gel strength |
|---|---|---|
| B1 | 0.320 g/cm$^2$/2-hrs | 3 |
| B2 | 0.255 g/cm$^2$/2-hrs | 3 |
| Comp B | 0.250 g/cm$^2$/2-hrs | 3 |

The results of the DMA showed that the the tangens delta of the compositions are at the same level for all three adhesives whereas the complex shear modulus G' [Pa] is slightly greater for samples B1 and B2 than for Comp B. No difference in leaching out was found.

Thus, it appears that the adhesives of the invention shows at least the same absorption of water retaining the same gel strength as the adhesive of the state of the art.

What is claimed is:

1. A pressure sensitive adhesive composition which is free from components of animal origin, is suitable for medical purposes and which, has a rubbery elastomeric base, said adhesive composition comprising a substantially homogeneous mixture of a) from 15 to 60% of a rubbery component, b) from 10 to 60% of a mixture of water soluble or water swellable hydrocolloids comprising a cellulose derivative, an amidated pectin and potato starch, c) from 0 to 50% of tackifier resin, d) from 0 to 15% of cohesive strengthening agent, e) from 0 to 10% of plasticizer, and f) from 0 to 5% pigment.

2. A pressure sensitive adhesive composition according to claim 1, which comprises a substantially homogeneous mixture of a) from 30 to 60% of a rubbery component, b) from 30 to 60% of a mixture of hydrocolloids wherein the cellulose derivative is carboxymethylcellulose (CMC), c) from 0 to 25% of tackifier, d) from 0 to 10% of cohesive strengthening agent, e) from 0 to 10% of plasticizer, and f) from 0 to 5% pigment.

3. A pressure sensitive adhesive composition as claimed in claim 1 wherein the mixture of hydrocolloids comprises CMC and amidated pectin.

4. A pressure sensitive adhesive composition as claimed in claim 1 wherein the mixture of hydrocolloids comprises CMC, amidated pectin and potato starch.

5. A pressure sensitive adhesive composition as claimed in claim 1 wherein the cohesive strengthening agent is a physically cross-linked elastomer copolymer of styrene, a chemically cross-linked natural or synthetic rubbery elastomer or a rubbery homopolymer.

6. A method which comprises securing to skin a member selected from the group consisting of an ostomy appliance, a wound dressing, a wound drainage bandage, a device for collecting urine, an orthosis and a prosthesis with a composition wherein the composition is a pressure sensitive adhesive composition according to claim 1.

7. An ostomy appliance useful for placing on the abdomen of a patient for collecting discharge of visceral contents, which appliance comprises an adhesive composition and wherein the adhesive composition is a pressure sensitive adhesive composition as claimed in claim 1 and the mixture of hydrocolloids comprises CMC, amidated pectin and potato starch.

8. A mixture of hydrocolloids which is free from components of animal origin and is suitable for inclusion in a pressure sensitive skin-friendly adhesive, said mixture comprising a cellulose derivative, amidated pectin and potato starch.

9. A mixture of hydrocolloids as claimed in claim 8 wherein the cellulose derivative is CMC.

10. A mixture of hydrocolloids as claimed in claim 8 which consists essentially of an amidated pectin, potato starch and a cellulose derivative.

11. A method of sealing an ostomy appliance around an ostomy which comprises using an adhesive composition as claimed in claim 2.

12. A mixture of hydrocolloids as claimed in claim 10 wherein the cellulose derivative is CMC.

13. A pressure sensitive adhesive composition as claimed in claim 1 which comprises tackifier resin.

14. A pressure sensitive adhesive composition as claimed in claim 13 which comprises cohesive strengthening agent.

15. A pressure sensitive adhesive composition as claimed in claim 14 which comprises plasticizer.

16. A pressure sensitive adhesive composition as claimed in claim 15 which comprises pigment.

17. A pressure sensitive adhesive composition as claimed in claim 1, wherein the mixture of hydrocolloids consists essentially of a cellulose derivative, an amidated pectin and potato starch.

* * * * *